US005688674A

United States Patent [19]
Choi et al.

[11] Patent Number: 5,688,674
[45] Date of Patent: Nov. 18, 1997

[54] CONTINUOUS FERMENTATION PROCESS FOR THE PRODUCTION OF METABOLITIES USING A MOVING FILTER

[75] Inventors: Cha-Yong Choi, Olympic Family Apt. 223-1301, 150, Moonjeong 2-dong, Songpa-ku, Seoul, Rep. of Korea, 138-202; Young-Lyeol Yang, Seoul, Rep. of Korea

[73] Assignee: Cha-Yong Choi, Seoul, Japan

[21] Appl. No.: 607,482

[22] Filed: Feb. 27, 1996

[30] Foreign Application Priority Data

Sep. 29, 1995 [KR] Rep. of Korea ............... 95-32844

[51] Int. Cl.⁶ ................. C12P 7/14; C12P 7/06; C12P 7/08; C12P 7/10
[52] U.S. Cl. ............ 435/162; 435/161; 435/163; 435/165; 435/803; 435/913; 435/940; 435/942
[58] Field of Search ................. 435/161, 162, 435/163, 165, 813, 913, 940, 942

[56] References Cited

U.S. PATENT DOCUMENTS

| 4,376,163 | 3/1983 | Ehnstrom | 435/162 |
| 4,460,687 | 7/1984 | Ehnstrom | 435/161 |

*Primary Examiner*—John W. Rollins
*Assistant Examiner*—Christopher R. Tate
*Attorney, Agent, or Firm*—Anderson Kill & Olick, P.C.

[57] ABSTRACT

A metabolite, e.g., ethanol, is continuously produced from low cost carbohydrate substrates by a process which comprises pulverizing the carbohydrate substrate; liquefying and saccharifying the pulverized substrate; continuously fermenting the lique-saccharified substrate in a fermentor equipped with a moving filter, in the presence of flocculent biological cells maintained at a concentration ranging from 90 to 160 g/l by using the moving filter and a culture medium to produce a fermentation product mixture; and recovering the desired metabolite from the fermentation product mixture.

15 Claims, 6 Drawing Sheets

CONTINUOUS FERMENTATION PROCESS FOR THE PRODUCTION OF METABOLITES USING A MOVING FILTER

FIELD OF THE INVENTION

The present invention relates to a process for producing metabolites from low cost substrates; and, more particularly, to a highly efficient and economical continuous fermentation process for producing metabolites by employing flocculent biological cells and a fermentor equipped with a moving filter.

BACKGROUND OF THE INVENTION

A wide range of metabolites including alcohol have been used for various purposes such as bioenergy, e.g., vehicular fuel; pharmaceuticals, e.g., antibiotics, anticancer drugs, proteins and hormones; food, e.g., amino acids, liquor, nucleotides and related products, lactic acid, citric acid and organic acids; industrial chemicals; and environment-related products.

The commercial production of metabolites, e.g., ethanol, has been carried out by conventional batch fermentation processes which generally suffer from low productivity. Therefore, there have been keen interests in developing an efficient continuous fermentation process capable of substantially lowering the production cost, and particularly using a low-cost raw material to make the price of the final product competitive.

Hitherto, there have been reported several types of continuous fermentation processes, including a process for producing ethanol in a tower-type fermentor packed with flocculated yeast cells. In theses processes, however, high-cost raw materials such as purified molasses and glucose are used as the carbohydrate substrate, while the reported reactor performances are generally unsatisfactory due to various deficiencies such as low productivity, low cell density, instability of the packed bed caused by hydrodynamic factors, and the tendency of cell aggregates to break up under a poor nutrient condition.

The performance of a continuous metabolite production reactor may be evaluated based on three criteria: productivity, product stream quality and long-term stability.

The productivity, expressed by grams of the metabolite produced per hour per liter of working reactor volume, may be calculated by multiplying the metabolite product concentration in the product stream (g/l) by the dilution rate which is defined as the volume of substrate introduced to the reactor per hour per working volume of the reactor. The key for increasing the productivity lies in increasing the cell density, i.e., the concentration of the active cell aggregates used for carrying out the fermentation.

The product stream quality is determined by the metabolite product concentration as well as the concentration of unreacted substrate in the effluent. As the cost for separating the metabolite product from the product stream increases with a decrease in the product concentration, it is desirable to raise the metabolite concentration in the product stream as high as possible. On the other hand, the presence of unreacted substrate not only reduces the overall process efficiency but also induces the problem of cell bleeding which is caused by $CO_2$ generated by fermentation of the residual substrate.

The long-term stability, which is perhaps the most important criterion in deciding the viability of a particular reactor system, may be achievable only when a high cell density can be sustained over a sufficient period of time under a set operational condition of the reactor. If the cell density decreases or fluctuates with time for any reason, commercial implementation of the system may become difficult.

The prior art processes using the tower-type continuous reactor have failed to meet one or all of the above criteria, rendering them unsuitable for commercial applications. For instance, Netto et al. attempted continuous ethanol production from corn hydrolysate using a tower fermentor packed with flocculated yeast for a period of 300 hours. However, they could not raise the dilution rate beyond 0.3 $hr^{-1}$ because of a rapid fall of the cell density with the lapse of time from the initial level of 80–90 g/l. The maximum productivity achieved was shown to be only 18.4 g of ethanol per hour per liter of reactor volume while the residual glucose concentration amounted to 2.3 g/l. Even under this poor performance condition, they still experienced the problem of an operational instability due to the deflocculation of cells (see Netto et al., "Ethanol Fermentation by Flocculating Yeast: Performance and Stability Dependence on a Critical Fermentation Rate", *Biotechnology Letters*, 7, 1985, pp 355–360).

Limtong et al. also employed flocculating yeast to produce ethanol continuously from glucose at a relatively high cell density of 70–90 g/l. However, they had to lower the glucose substrate concentration in the feed in order to suppress the residual glucose concentration below 1 g/l, thus limiting the attainable ethanol concentration to below 6.6%. They also experienced a rapid drop in the cell concentration when the dilution rate was increased beyond 0.5 $hr^{-1}$ (see Limtong et al., "Continuous Ethanol Production by a Concentrated Culture of Flocculating Yeast", *J. Ferment. Technol.*, 62, 1984, pp 55–62).

Further, Chen produced ethanol at a concentration of 7.7% and 3.1% from glucose and molasses, respectively, by using a tower-type fermentor. Although Chen achieved a relatively high cell concentration at a high dilution rate, e.g., 90–100 g/l at 0.7 $hr^{-1}$, these were attained only in short-term studies and the issue of the long-time stability was not addressed. Moreover, the residual glucose concentration in the case of using molasses was very high, i.e., 62 g/l (see C. S. Chen, "Ethanol Fermentation Using Self-aggregating Yeast", *Proceedings of YABEC '95*, 1995, pp 24–38).

Thus, despite the use of high-cost raw materials such as purified molasses and glucose, the prior studies have not succeeded in developing an efficient continuous process for producing ethanol because of the occurrence of the variety of problems described above.

In order to make the process more economical, therefore, there has continued to exist a need to develop a commercially viable continuous fermentation process which is capable of utilizing low-cost raw materials, e.g., untreated molasses, starch-containing materials such as tapioca, sweet potato and grains, and cellulose- and xylose-containing materials such as wood, corn and other plant stovers. When such material is used as the feed substrate, however, each of the problems mentioned above is expected to become even further aggravated, and, moreover, there may emerge additional problems caused by suspended solid particles remaining in the lique-saccharified substrate. Complete removal of such suspended particles is not achievable by a conventional centrifugation or filtration method, and a substrate solution containing such solid particles, when fed to a tower-type continuous reactor, would cause such problems as increased culture medium viscosity due to the buildup of solid particles, increased mass transfer resistance, channeling, deflocculation of cell aggregates, low cell density by cell bleeding and lowering of the decanter efficiency.

SUMMARY OF THE INVENTION

Accordingly, it is an object of the present invention to provide a process which is substantially free of the problems mentioned above and capable of continuously producing a metabolite from low-cost substrates, in a high productivity and economic fashion, by way of employing flocculent biological cells and a fermentor equipped with a moving filter.

In accordance with one aspect of the present invention, there is provided a continuous process for producing a metabolite from a carbohydrate substrate which comprises: (A) pulverizing the carbohydrate substrate; (B) liquefying and saccharifying the pulverized substrate; (C) fermenting the lique-saccharified substrate in a fermentor equipped with a moving filter, in the presence of flocculent biological cells maintained at a concentration ranging from 90 to 160 g/l by using the moving filter and a culture medium to produce a fermentation product mixture; and (D) recovering the metabolite from the fermentation product mixture.

BRIEF DESCRIPTION OF DRAWINGS

The above and other objects and features of the present invention will become apparent from the following description, taken in conjunction with the accompanying drawings, wherein.

DETAILED DESCRIPTION OF THE INVENTION

Figure 1:
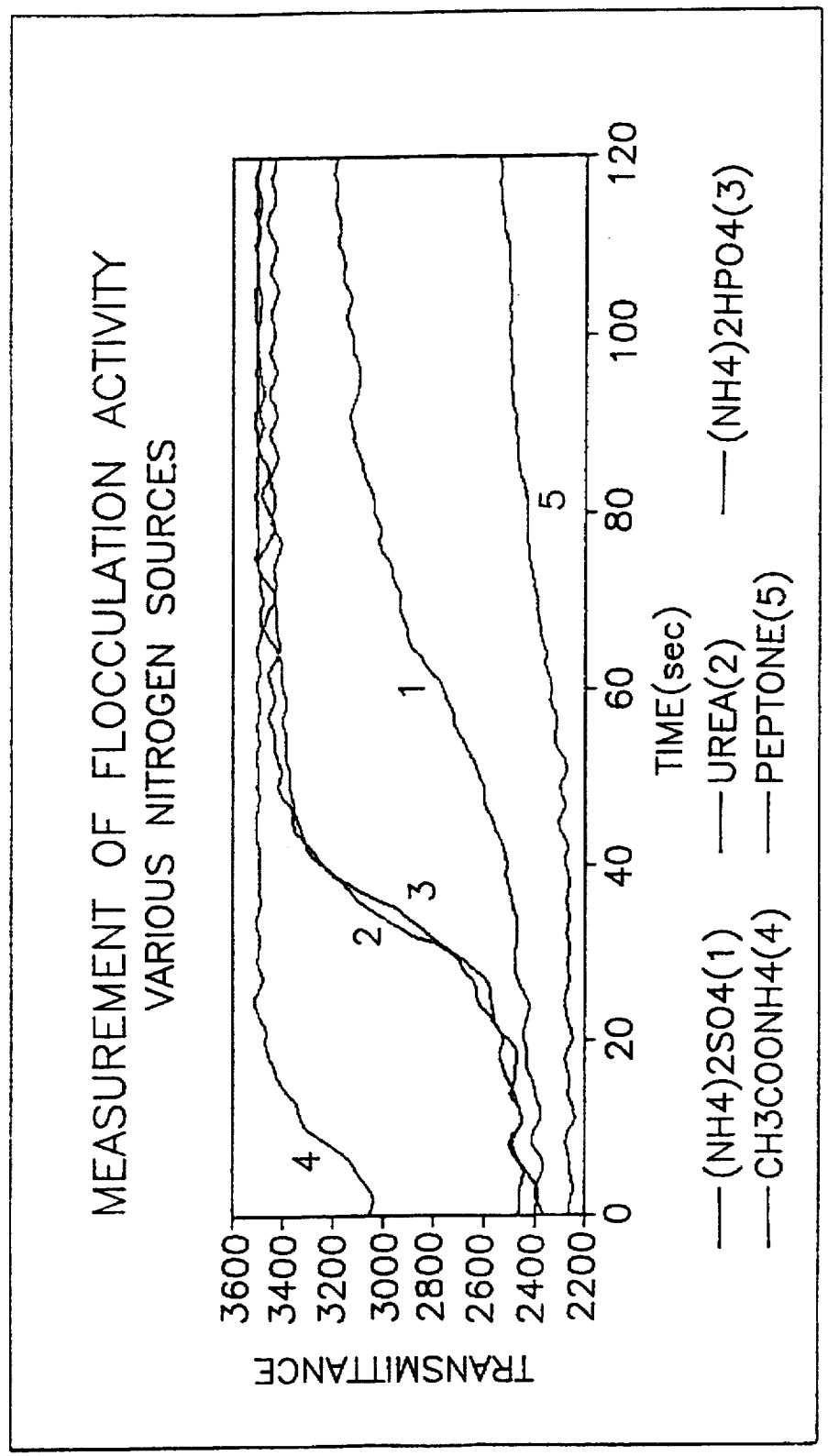
FIG. 1 shows the effect of various nitrogen compounds on the flocculation rate and the sedimentation velocity of flocculent biological cells.

In accordance with the present invention, there is provided an economical process for continuously producing a metabolite by fermenting a low cost carbohydrate substrate in a continuously stirred tank reactor equipped with a moving filter wherein a high concentration of flocculent biological cells is maintained by using the moving filter.

(i) Pulverization and liquefaction-saccharification

The carbohydrate substrate may be preferably pulverized to a substrate powder. The carbohydrate substrates which may be used in the present invention include molasses, industry-grade glucose, starch-containing materials such as tapioca, potato, sweet potato and grains, and cellulose- and xylose-containing materials such as wood, corn stovers, cane stovers and other agricultural wastes. It is preferred to pulverize the carbohydrate substrate until the particle size thereof lies within the range of 10 to 1,000 μm using a conventional equipment, e.g., ball mill.

The powdered carbohydrate substrate may be then liquefied and saccharified by using a conventional method known to ordinary persons skilled in the art. For example, the liquefaction-saccharification may be carried out with water and enzymes, which are capable of hydrolysing the substrate to glucose, at an elevated temperature, e.g., 50° to 95° C., for several hours. Representatives of such useful enzyme include amylase, glucoamylase, cellulase, cellobiase and a mixture thereof. The lique-saccharified substrate may have a glucose concentration ranging from 140 to 300 g/l and a solid particle concentration of less than 60% (v/v), wherein the suspended solid particles may have a particle size distribution ranging from 1 to 1,000 μm, more preferably 1 to 100 μm.

Subsequently, the lique-saccharified substrate may be directly introduced into a fermentor, or if necessary, may be subjected to a liquid/solid separation procedure to remove relatively large solid particles present therein before being introduced to the fermentor. This solid particles separation may be carried out by employing a simple device such as a decanter, low speed centrifuge or membrane. The feed to the fermentor preferably has a suspended solid content of less than 20% (v/v).

(ii) Fermentation

In accordance with the present invention, the fermentation process is carried out in a fermentor equipped with a moving filter in the presence of flocculent biological cells and a culture medium. The flocculent cells which may be used in the present invention include those having the flocculating property, which may be procaryotic or eucaryotic and be found in nature or produced by a gene manipulation technique. Suitable cells may be selected depending on the desired metabolic product; and representatives of such cells include Streptomyces species, Aspergillus species, yeast and the like. In the inventive process, the concentration of the cells in the fermentor during the continuous fermentation procedure is maintained at a range of 90 to 160 g/l.

The moving filter in the fermentor may be of a screen or a membrane with an opening size ranging from 10 to 4,000 mesh, preferably 50 to 2,000 mesh, and may be placed in a proper position inside the fermentor. The filter in accordance with the present invention makes it possible to maintain the cell concentration at a high level by way of blocking the passing of the flocculent cells while allowing the suspended solid particles to pass freely therethrough.

The moving filter may be installed, if desired, outside the fermentor, e.g., in a sedimentor suitably connected to the fermentor. The filter may be shaped in a variety of form such as cylinder, basket, plate or disk. Multiple filters may also be installed in an arrangement suitable for a particular need.

The moving filter may be equipped with an agitator e.g., a screw, ribbon or intermig type, to generate a various mode of liquid motions including rotation, reciprocation, vibration, swirling, gyration, and a combination thereof. Further, the filter may be optionally equipped with back-flushing accessories to deal with a process upset that might cause a clogging problem. The cells and solid particles that may deposit on the surface of the filter may be removed by a conventional method, i.e., application of vibration, ultrasonic waves, gas jets and the like.

The fermentation process may be carried out at a condition suitably chosen depending on the desired metabolite product, types of biological cells, culture medium and the like, as is well known to the ordinaly person skilled in the art.

The culture medium may be employed to adjust the growth, the flocculating property and the aggregate size of the cells. The medium may include a nitrogen containing compound and, if required, additional compounds in trace amounts depending on the glucose concentration of the lique-saccharified substrate. Illustratives of the nitrogen containing compounds include ammonium phosphate mono- or dihydride, ammonium sulfate, ammonium nitrate, ammonium acetate, urea, yeast extract, peptone or a mixture thereof, and representatives of the additional compounds include sodium or potassium dihydrogen phosphate, disodium or dipotassium hydrogen phosphate, sodium chloride, calcium chloride, ferrous sulfate, magnesium sulfate or a mixture thereof.

Although the inventive fermentation may be carried out in a continuous mode, a fill-draw type sequencing batch reactor (SBR) operation may also be used during the start-up period, or when it is necessary to rapidly raise the cell density and/or to adjust the cell floc size during the steady state operation. To accelerate the fermentation rate, air may be introduced to the fermentor by a suitable means, e.g., an air sparger, which may be installed in the fermentor.

The SBR mode of operation may be conducted as follows. The feed solution and the nutrients are introduced into a space external to the filter and the fermentation product is taken out from the inside of the moving filter. The fermentor is first inoculated with suitable biological cells at a concentration ranging from 3 to 4 g/l. The cell culture may be performed in a batch mode followed by 3 to 5 cycles of fill-draw SBR operations, thereby increasing the cell concentration to a desired level, e.g., 15 to 20 g/l. At this point, the cells flocculate to form cell flocs, which continue to grow. Recycling of the cells from inside to outside of the moving filter may be conducted during the SBR operation. When the cell concentration reaches the desired level, the operation is switched to a continuous mode and the dilution rate of the substrate is increased gradually until the cell concentration reaches above 100 g/l. Finally, a steady-state continuous fermentation operation is carried out at a dilution rate of the substrate ranging from 0.5 to 2 $hr^{-1}$, while maintaining the cell concentration at a range of about 90 to 160 g/l.

In the fermentation process, multiple fermentors may be employed in order to further increase the productivity of the desired metabolite product.

(iii) Purification

The fermentation product mixture is then subjected to a series of separation processes to recover the desired metabolite product. For example, the mixture may be first introduced into one or more sedimentors wherein bled cells are allowed to settle. Such cells may be removed or recycled to the fermentor, and the supernatant which may contain solid materials is drawn out for a conventional separation process, e.g., distillation, adsorption or the like.

Preferred Embodiment of the Invention

In accordance with the preferred embodiment of the present invention, ethanol may be continuously produced from a low cost carbohydrate substrate in a high productivity.

Specifically, the carbohydrate substrate is pulverized, and then lique-saccharified. The lique-saccharified substrate preferably has a glucose concentration ranging from 14 to 30% and solid particles content of less than 60% (v/v), and, more preferably, less than 20% (v/v), wherein the size of solid particles ranges from 10 to 1,000 µm.

The lique-saccharified substrate is then fermented in a fermentor equipped with a moving filter in the presence of flocculent biological cells maintained at a concentration ranging from 90 to 160 g/l by using the moving filter and a culture medium to produce a fermentation product mixture.

In the ethanol fermentation process, as the biological cells, a yeast, preferably *Saccharomyces cerevisiae*, *Saccharomyces diastaticus* and *Saccharomyces uvarum*, may be used, while *Saccharomyces uvarum* is most preferred.

The ethanol fermentation may be carried out at a temperature ranging from 4° to 40° C., more preferably from 15° to 35° C., and at a pH ranging from 3.5 to 9, more preferably from 4 to 8, while the filter may be rotated at a rate less than 1,000 rpm, more preferably less than 500 rpm. The components of the culture medium may be employed in their respective amount ranging from 0 to 40 g/l.

In the case of ethanol production in accordance with the inventive fermentation process, the ethanol concentration reaches a level of 7 to 10% by a single stage fermentation, which may be increased further beyond 10% by a suitable combination of a multiple number of fermentors.

Subsequently, ethanol is easily recovered from the supernatant of the fermentation product mixture by a suitable separation method, e.g., a distillation or adsorption process.

The productivity of ethanol in accordance with the inventive fermentation process can reach the level of 70 g/hr/liter of the fermentor volume or more while retaining the yield close to the theoretical value, i.e., about 94%, which is much higher than the productivity achievable by the prior art methods. The cell concentration in the fermentor can be maintained at a level as high as about 110 to 130 g/l; the continuous operation can be sustained for a long period time, e.g., 2 months or longer; and the process is substantially free from the risk of contamination by foreign microorganisms.

Examples

The following Examples are intended to illustrate the present invention more specifically, without limiting the scope of the invention.

Reference Example 1: Dependency of the cell flocculation property on the type of nitrogen source A lique-saccharified substrate solution containing 150 g/l of glucose and 1.5% (v/v) of solid particles having a size distribution ranging from 10 to 1,000 pm was mixed with distilled water in a ratio of 1:3. 100 ml of the resultant solution was charged into a 300 ml flask and a nitrogen source to be tested was added thereto in an amount corresponding to a concentration of 3 g/l. Thereafter, to the flask were added 3 g/l of *Saccharomyces uvarum* (ATCC 28097) cell and 1 g/l of $KH_2PO_4$. The cells were cultivated at 30° C. on a shaking incubator at 200 rpm. After 14 hours, the flocculation activity of the cell was determined by measuring the light transmittance at 7 cm height of a test sedimentor using a cadmium sulfide (CdS) photoconductivity cell. As shown in FIG. 1, the best result was obtained with ammonium acetate, i.e., the sedimentation was completed within 15 seconds.

Reference Example 2: Effect of pH on flocculation

Figure 2:
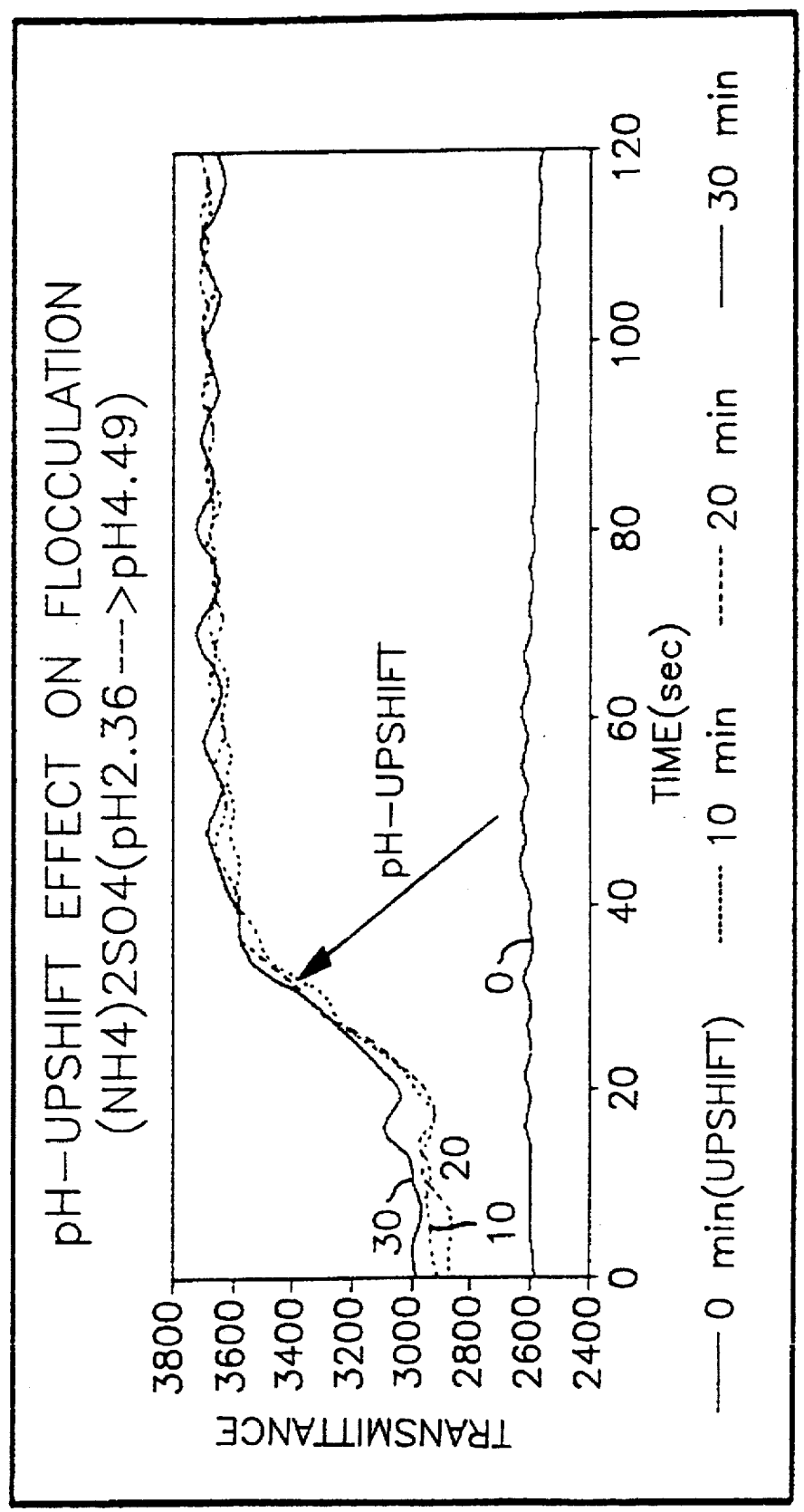
FIG. 2 presents the effect of pH change on the flocculation rate of the cells.

A lique-saccharified substrate solution containing 150 g/l of glucose and 1.5% (v/v) of solid particles having a size distribution ranging from 10 to 1,000 µm was mixed with distilled water in a ratio of 1:3 at 30° C. 100 ml of the resultant solution was charged into a 300 ml flask, and added thereto were 3 g/l of ammonium sulfate as a nitrogen source, 3 g/l of *Saccharomyces uvarum* (ATCC 28097) cell, and 1 g/l of $KH_2PO_4$. After 16 hours, pH of the solution was changed from 2.36 to 4.49 by adding an aqueous KOH solution, and then the flocculation activity was observed using a cadmium sulfide(CdS) photoconductivity cell. The results illustrated in FIG. 2 show that the pH upshift greatly improves the flocculation activity of the cells.

Reference Example 3: SBR (Sequencing Batch Reactor) operation

Figure 3:
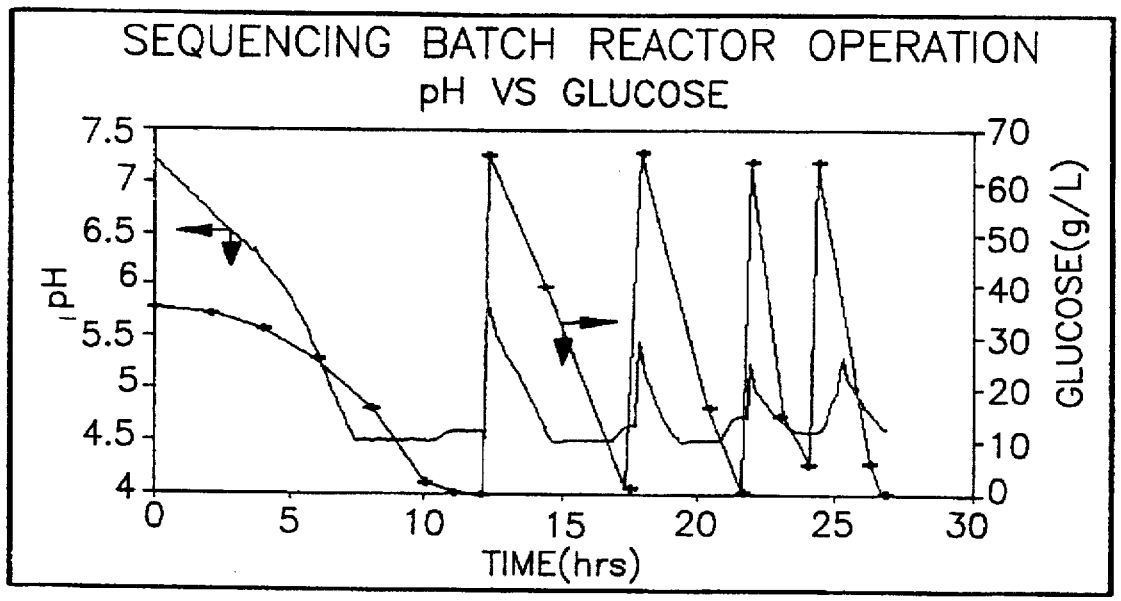
FIG. 3 provides the results of the sequencing batch reactor operation according to Reference Example 3 hereof.
Figure 5:
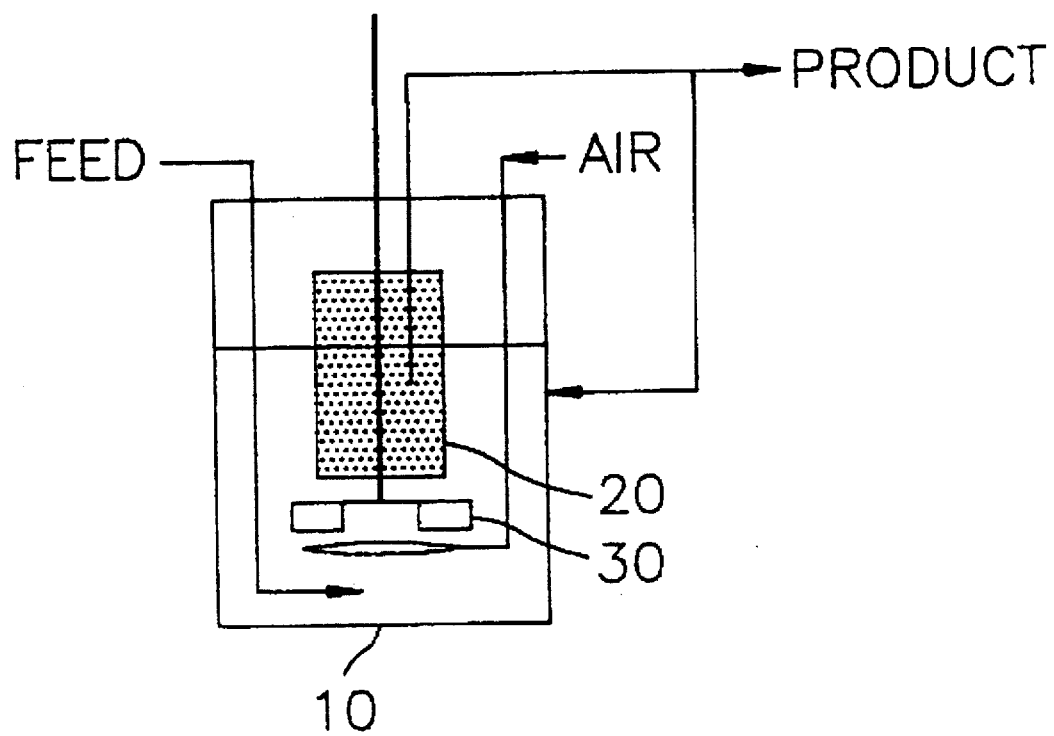
FIG. 5 depicts a schematic longitudinal sectional view of an embodiment of a fermentor equipped with a moving filter for use in the inventive fermentation process.

A lique-saccharified substrate solution containing 150 g/l of glucose and 1.5% (v/v) of solid particles was mixed with 12 g/l of ammonium acetate and 3 g/l of $KH_2PO_4$. The resulting mixture was added to a 2 L fermentor (BioFlo IIc, NBS, USA) whose basic features are schematically shown in FIG. 5. Batch and SBR operations were conducted at 30° C., while rotating the agitator at 200 rpm, aerating at 0.5 vvm, and maintaining pH at 4.5. A pH upshift was observed upon the depletion of the glucose in the reaction mixture during the batch culture. Based on this characteristic pattern of pH change, the timing for the drawing-filling procedure for an SBR operation was determined. The results of carrying out four drawing-filling cycles are shown in FIG. 3, wherein the exchange volume was 1 l and the flocculent cell used was *Saccharomyces uvarum* (ATCC 28097).

Example 1: Liquefaction-saccharification

Figure 4:
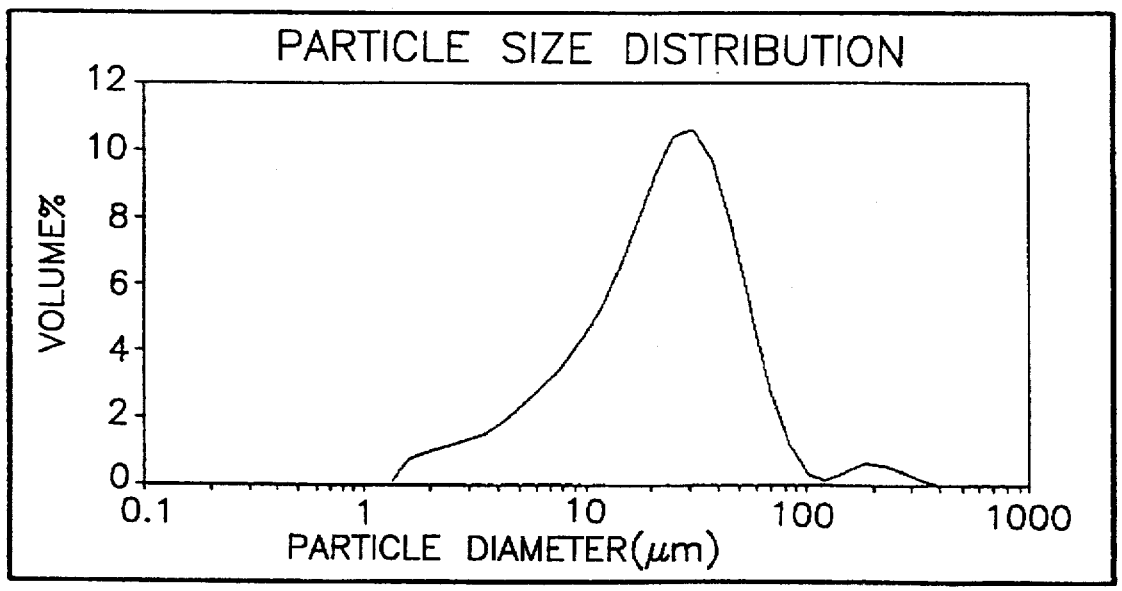
FIG. 4 exhibits the size distribution of particles remaining in the filtrate after centrifuging the lique-saccharified substrate by a low speed laundry decanter.

Tapioca was ball milled to obtain a powder having 10 to 1,000 μm particle size. In 300 L tank, 25 kg of the tapioca powder was mixed with 100 kg of hot water, and the resulting mixture was transferred to a 200 L tank and liquefied at 90° C. for 2 hours after adding 15 ml of α-amylase (Termamyl 120L, Novo) to the mixture. The saccharification step was then conducted at 60° C. for 10 to 12 hours by adding 37.5 ml of glucoamylase (SPEZYME GA 300N, Genencor), 37.5 ml of cellulase (Celluclast 1.5L, Novo) and 7.5 ml of cellobiase (NOVOZYME 188, Novo) to the liquefied tapioca solution. The solid particles in the lique-saccharified tapioca solution amounted to 45% (v/v) and had a particle size in the range of 10 to 600 μm, as measured using a particle size analyzer (a product of Malvern Instruments, United Kingdom). The glucose concentration in the lique-saccharified solution was 150 g/l. The lique-saccharified solution was then centrifuged using a low-speed laundry type decanter and the solid particles remaining in the filtrate had an average particle size of 20 μm as shown in FIG. 4.

This filtrate having a solid particle content of 10% (v/v) and a glucose concentration of 150 g/l was employed as a feed solution to the subsequent fermentation process.

Example 2: Fermentation

Referring to FIG. 5, 500 ml of the feed solution obtained in Example 1 was introduced to a 3 L fermentor (10) (BioFlo IIc, NBS, USA) equipped with a cylindric screen filter (20) having an opening size of 325 mesh which was allowed to move with an agitator (30). The working volume of the fermentor was 2 L. To the fermentor was added 4% (w/v) of urea as nitrogen source and 1% (w/v) of $KH_2PO_4$.

Figure 6:
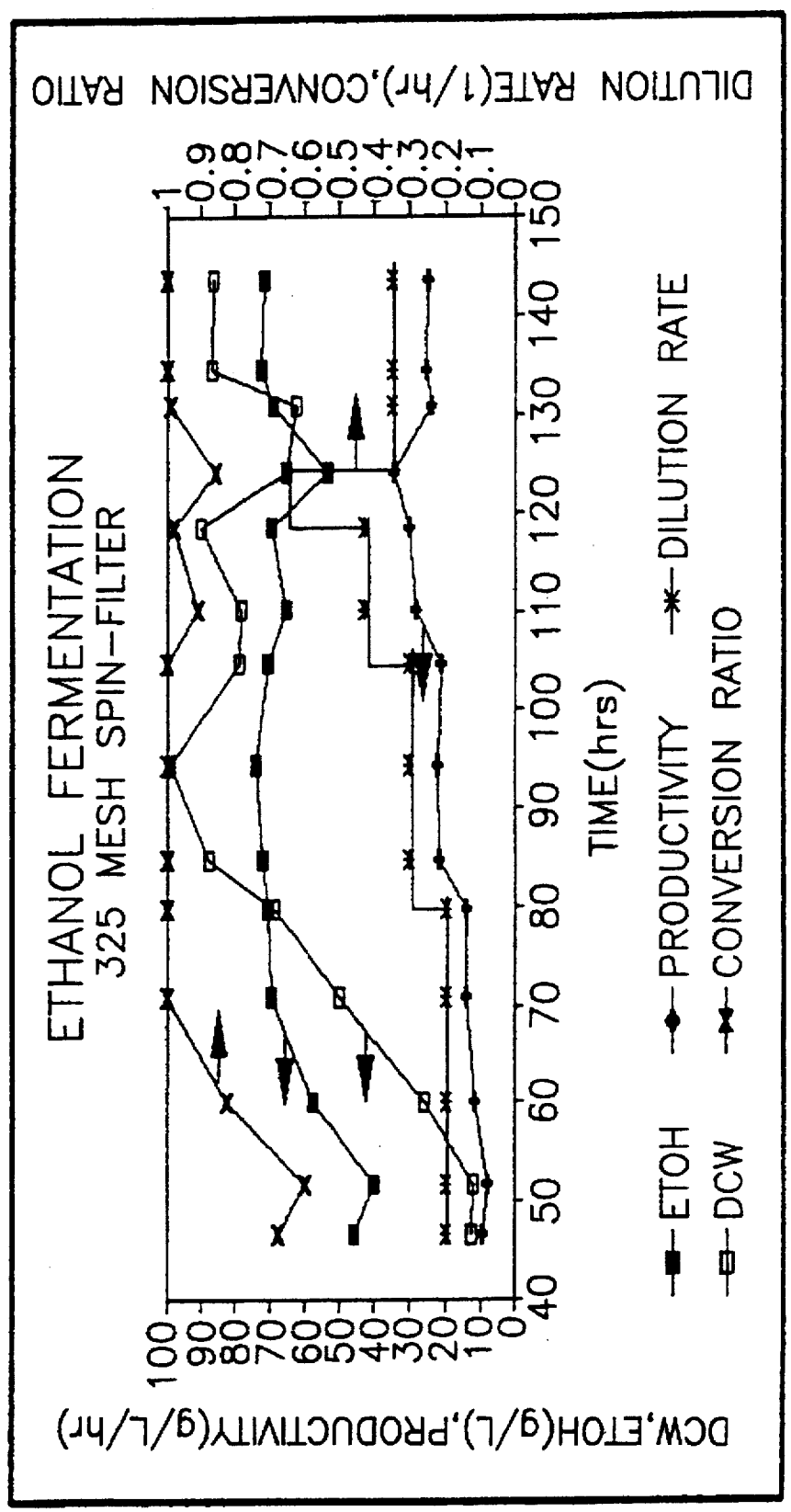
FIG. 6 describes the results of the continuous fermentation run conducted in accordance with Example 2 hereof.

The mixture in the fermentor was then inoculated with 0.4 g of *Saccharomyces uvarum* (ATCC 28097) and cultured in a batch mode at 30° C. for 16 hours, followed by conducting 4 SBR cycles to increase the cell concentration to 18 g/l, when cell pellets started to form. During the SBR operation, recycling of the cells from inside to outside of the moving filter was conducted. Subsequently, the operation was switched to a continuous mode by continuously introducing the feed solution obtained in Example 1 to outside of the filter in the fermentor under a condition of 30° C., agitation rate of 200 rpm, aeration rate of 0.5 vvm, and pH 4.5, and the dilution rate of the substrate was gradually increased, as shown in FIG. 6. During the course of this experiment, it was confirmed that there was no ethanol or glucose concentration gradient across the filter.

The results of this continuous fermentation operation are shown in FIG. 6.

Example 3: Long-term continuous operation at high dilution rates

Figure 7:
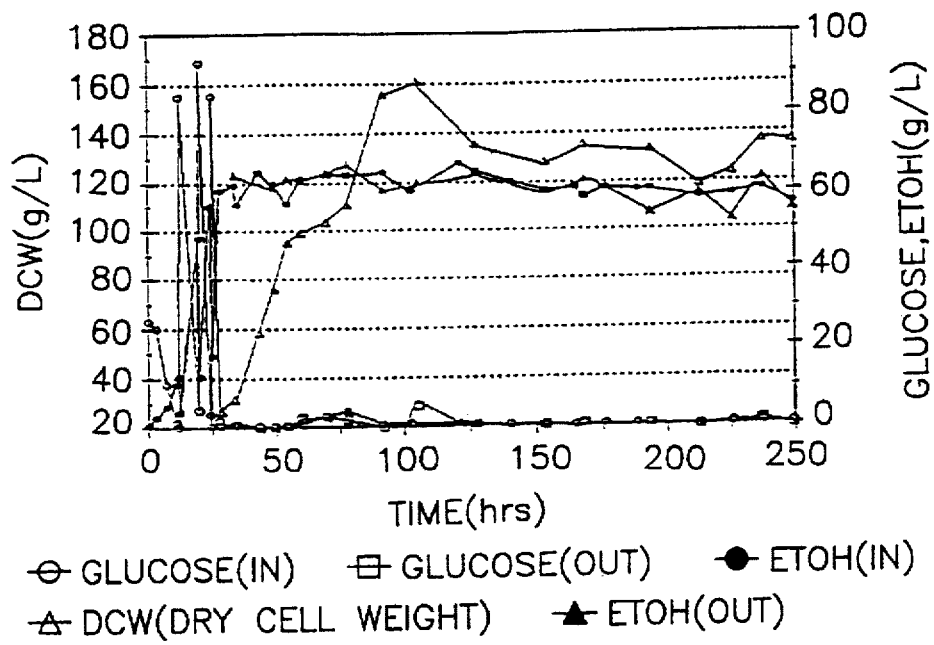
FIG. 7 offers the results of the long-term continuous fermentation run conducted in accordance with Example 3 hereof.

The procedure of Example 2 was repeated except that a 6:1 mixture of urea and ammonium acetate, instead of urea, was employed as the nitrogen source to conduct a long-term continuous operation at a dilution rate of 0.5 $hr^{-1}$. The results (FIG. 7) show that a steady cell density in the range of 120 to 140 g/l as well as a steady ethanol concentration in the range of 6.0 to 6.5% (w/v), could be maintained throughout the length of the operation, while the residual glucose concentration was practically nill.

Example 4: Productivity

Figure 8:
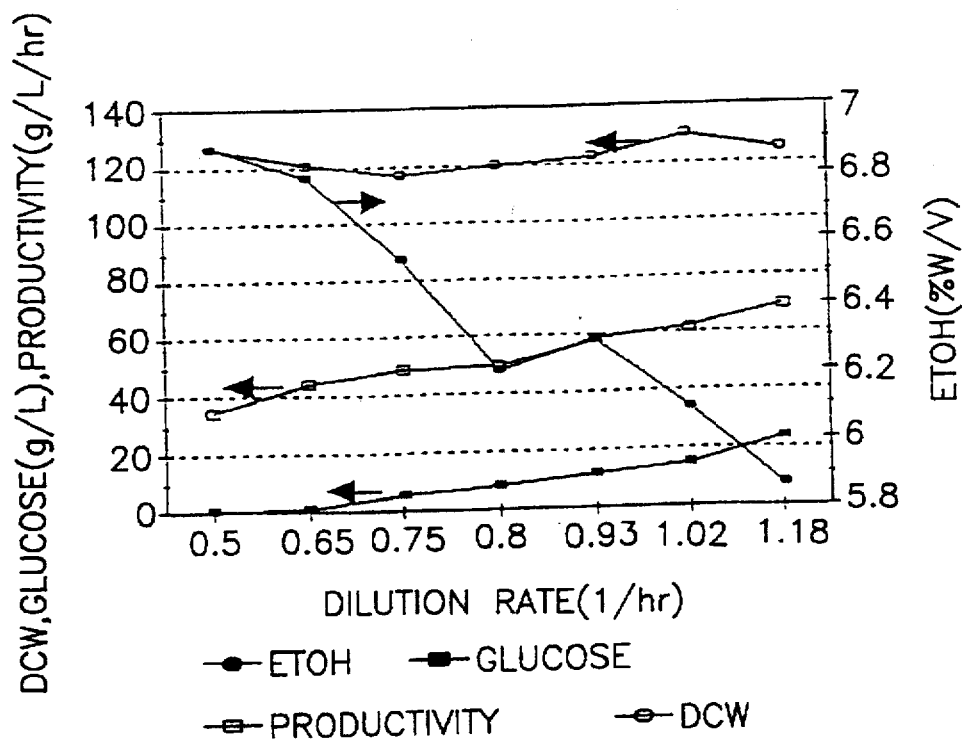
FIG. 8 sets forth the results of the long-term continuous fermentation run conducted at high dilution rates in accordance with the present invention.

In order to investigate the productivity at a high dilution rate of the inventive process, the procedure of Example 2 was repeated except that the dilution rate was varied from 0.5 to 1.2 $hr^{-1}$, and the results in FIG. 8 show that the productivity increases with the dilution rate of the substrate to reach 70 g of ethanol/l.hr at a dilution rate of 1.18 $hr^{-1}$, while a steady cell concentration of 110 to 130 g/l was maintained throughout the experiment.

The results of foregoing Examples 1 to 4 demonstrate that the inventive process has all the desirable features of high productivity, excellent fermentation product quality and satisfactory long-term stability, and that these results are clearly superior to those achievable by the prior art methods.

While the invention has been described in connection with the above specific embodiments, it should be recognized that various modifications and changes may be made by those skilled in the art to the invention which also fall within the scope of the invention as defined by the appended claims.

What is claimed is:

1. A continuous process for producing a metabolite from a carbohydrate substrate which comprises the steps of: (A) pulverizing the carbohydrate substrate; (B) liquefying and saccharifying the pulverized substrate; (C) continuously fermenting the lique-saccharified substrate in a fermentor, in the presence of biological cells and a culture medium to produce a fermentation product mixture; and (D) recovering the metabolite from the fermentation product mixture; wherein the fermentor is equipped with a moving filter having an opening size ranging from 50 to 2,000 mesh and the biological cells are flocculent cells maintained at a concentration ranging from 90 to 160 g/l by the moving filter during the fermentation step.

2. The process of claim 1, wherein the liquefaction-saccharification in step (B) is carried out by adding water and enzymes to the pulverized substrate and maintaining the resultant mixture at a temperature ranging from 50° to 95° C.

3. The process of claim 2, wherein the lique-saccharified substrate obtained from step (B) has a glucose concentration ranging from 140 to 300 g/l and solid particles content of less than 60% (v/T), with the solid particles having a size distribution ranging from 1 to 1,000 μm.

4. The process of claim 2, wherein the enzyme employed in step (B) is selected from the group consisting of amylase, glucoamylase, cellulase, cellobiase and a mixture thereof.

5. The process of claim 1, wherein the lique-saccharified substrate obtained from step (B) is passed through a solid/liquid separator so as to remove a major portion of the solid particles therefrom prior to feeding the substrate to the fermentor.

6. The process of claim 5, wherein the lique-saccharified substrate has solid particles content of less than about 20% (v/v).

7. The process of claim 1, wherein the filter is of a screen or membrane type.

8. The process of claim 1, wherein the recovery in step (D) is carried out by removing bled cells from the fermentation product mixture to obtain a supernatant thereof and separating the metabolite from the supernatant.

9. The process of claim 8, wherein the cells removed are recycled to the fermentor.

10. The process of claim 1, wherein the metabolite is ethanol.

11. The process of claim 10, wherein the flocculent cells employed in step (C) are provided from a yeast.

12. The process of claim 11, wherein said yeast is selected from *Saccharomyces cerevisiae*, *Saccharomyces diastaticus*, *Saccharomyces uvarum* or a mixture thereof.

13. The process of claim 10, wherein the culture medium employed in step (C) includes a nitrogen containing compound selected from the group consisting of ammonium phosphate monohydride, ammonium phosphate dihydride, ammonium sulfate, ammonium acetate, ammonium nitrate, urea, yeast extract, peptone and a mixture thereof and additional compounds selected from the group consisting of sodium dihydrogen phosphate, potassium dihydrogen phosphate, disodium hydrogen phosphate, dipotassium hydrogen phosphate, sodium chloride, calcium chloride, ferrous sulfate, magnesium sulfate and a mixture thereof.

14. The process of claim 10, wherein the fermentation in step (C) is carried out at a temperature ranging from 4° to 40° C., at a pH ranging from 3.5 to 9, at a filter rotation rate of 1,000 rpm or less and at a dilution rate of the substrate ranging from 0.5 to 2.0 $hr^{-1}$.

15. The process of claim 14, wherein the fermentation is carried out at a temperature ranging from 15° to 35° C., at a pH ranging from 4 to 8 and at a filter rotation rate of below about 500 rpm.

* * * * *

UNITED STATES PATENT AND TRADEMARK OFFICE
CERTIFICATE OF CORRECTION

PATENT NO.    : 5,688,674
DATED         : November 18, 1997
INVENTOR(S)   : Cha-Yong Choi, et al It is certified that error appears in the above-identified patent and that said Letters Patent is hereby corrected as shown below:

Title page, item
[73] Assignee:  Cha-Yong Choi, Seoul, Rep. of Korea

Signed and Sealed this

Tenth Day of February, 1998

Attest:

BRUCE LEHMAN

Attesting Officer    Commissioner of Patents and Trademarks